United States Patent
Thong et al.

(10) Patent No.: US 7,627,811 B2
(45) Date of Patent: Dec. 1, 2009

(54) CONTENT-BASED SYNCHRONIZATION METHOD AND SYSTEM FOR DATA STREAMS

(75) Inventors: Jean-Manuel Van Thong, Arlington, MA (US); Leonidas Kontothanassis, Arlington, MA (US); David Goddeau, Watertown, MA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 627 days.

(21) Appl. No.: 11/072,036

(22) Filed: Mar. 4, 2005

(65) Prior Publication Data

US 2006/0200743 A1 Sep. 7, 2006

(51) Int. Cl.
*G06N 3/00* (2006.01)

(52) U.S. Cl. ..................................... 715/203
(58) Field of Classification Search ............. 715/500.1, 715/513, 517, 523, 530, 501.1, 234, 243, 715/254, 255, 203
See application file for complete search history.

(56) References Cited

U.S. PATENT DOCUMENTS

| | | | | |
|---|---|---|---|---|
| 4,991,032 A | * | 2/1991 | Staffer | 386/66 |
| 5,655,144 A | * | 8/1997 | Milne et al. | 715/500.1 |
| 6,249,319 B1 | * | 6/2001 | Post | 348/515 |
| 6,917,388 B2 | * | 7/2005 | Naka et al. | 348/537 |
| 6,999,504 B1 | * | 2/2006 | Amrany et al. | 375/222 |
| 2002/0018640 A1 | * | 2/2002 | Bolduc | 386/52 |
| 2005/0187766 A1 | * | 8/2005 | Rennillo et al. | 704/235 |
| 2006/0179403 A1 | * | 8/2006 | Kirkpatrick | 715/501.1 |
| 2006/0294453 A1 | * | 12/2006 | Hirata | 715/500.1 |

* cited by examiner

*Primary Examiner*—Kyle R Stork

(57) ABSTRACT

A computer method and system synchronizes one streaming data signal with another data signal. A subject data signal and working data signal are received. The working data signal has predefined coordinates in a coordinate system (e.g., time origin and unit sampling rate in a time coordinate system for audio). The subject data signal and working data signal are transformed into respective common representations. An alignment process aligns the respective transformed representations by matching the transformed representation of the working data signal to that of the subject signal. A re-synchronizer element transposes the predefined coordinates of the working data signal onto the subject signal in the aligned state of the respective transformed representations. As such, the subject data signal is synchronized to the coordinate system of the working data signal.

17 Claims, 5 Drawing Sheets

Overall document re-synchronization system

CONTENT-BASED SYNCHRONIZATION METHOD AND SYSTEM FOR DATA STREAMS

BACKGROUND OF THE INVENTION

Increases in data storage and network bandwidth capacity have made massive amounts of audio, video and images available on intranets and the Internet. However, digital media documents, though rich in content, generally lack structured and descriptive metadata that would allow indexing, random access and cross-linking. Content processing algorithms, such as segmentation, summarization or speech recognition, are commonly used to index and search digital media content. These algorithms can be run either on archived content or on live streams. One advantage of having a real time streaming implementation is the reduction of the delay between the end of the broadcast and the time the archived document is indexed and available for searching.

For audio and video, content analysis algorithms usually generate time-coded metadata such as topic boundaries or word transcriptions. The time-code should have a reference, or origin, so that the code can be used to randomly access the media document from the metadata information; for instance, given a query word, find the exact location where this word has been pronounced within an audio document. For archived documents, the origin is naturally the beginning of the audio/video file. For live streams, the produced time-coded metadata has to be re-synchronized with the archived material. One approach is to send a synchronization tag within the stream to indicate the beginning of the soon-to-be archived document. Unfortunately streaming protocols do not always allow such a tag within the stream.

Alternate approaches include:
using external clock synchronization,
inserting an explicit synchronization data packet into the data stream, and/or
inserting a well identified synchronization signal into the data stream.

External clock synchronization requires a priori agreement on the synchronization source and the existence of code to perform the synchronization (e.g., Audio Synchronization System, U.S. Pat. No. 5,655,144). It is usually an effective method, but data stream recorders may not have external clock synchronization. Moreover, the required precision of synchronization may be less than the clock difference after synchronization.

The same limitations apply when the synchronization is performed with synchronization data packets (e.g., Method and Apparatus for Finding a Correct Synchronization Point within a Data Stream, U.S. Pat. No. 6,249,319). This approach precludes the existence and use of specialized protocols.

Yet another approach inserts a well identified signal into the data stream and uses that pattern to synchronize clocks. This method is effective and is often used for analog signals. However, it cannot be used for audio live stream such as radio or video when broadcast over the Internet.

SUMMARY OF THE INVENTION

The present invention provides a method and system to address the problems of the prior art by using content segments to specify the start time and end time of an archived document. More generally, the preferred embodiment synchronizes two or more data signals from the same source. The signal to synchronize, also referred to herein as a subject data signal may be streaming data (such as streaming audio or video data, ECG or other physiological data and the like), sequence data (such as genomic sequences) and other series of data. The synchronizing signal, also referred to herein as a working data signal or segment, has predefined corresponding time or other coordinates. The two data signals are respectively transformed to a common representation. In their respective transformed representations, the data signals are matched against and ultimately aligned with one another. Once aligned, the time (or other) coordinates of the working segment can be transposed onto the subject data signal. As a result, the subject data signal is synchronized to the time system or other metric of the working segment.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

The preferred embodiment of the present invention addresses the problem of data stream re-synchronization for the purpose of archiving, indexing and algorithm evaluation. The description below focuses on live audio stream metadata re-synchronization for textual transcription and indexing. The method can be applied to other domains further discussed later.

Figure 1:
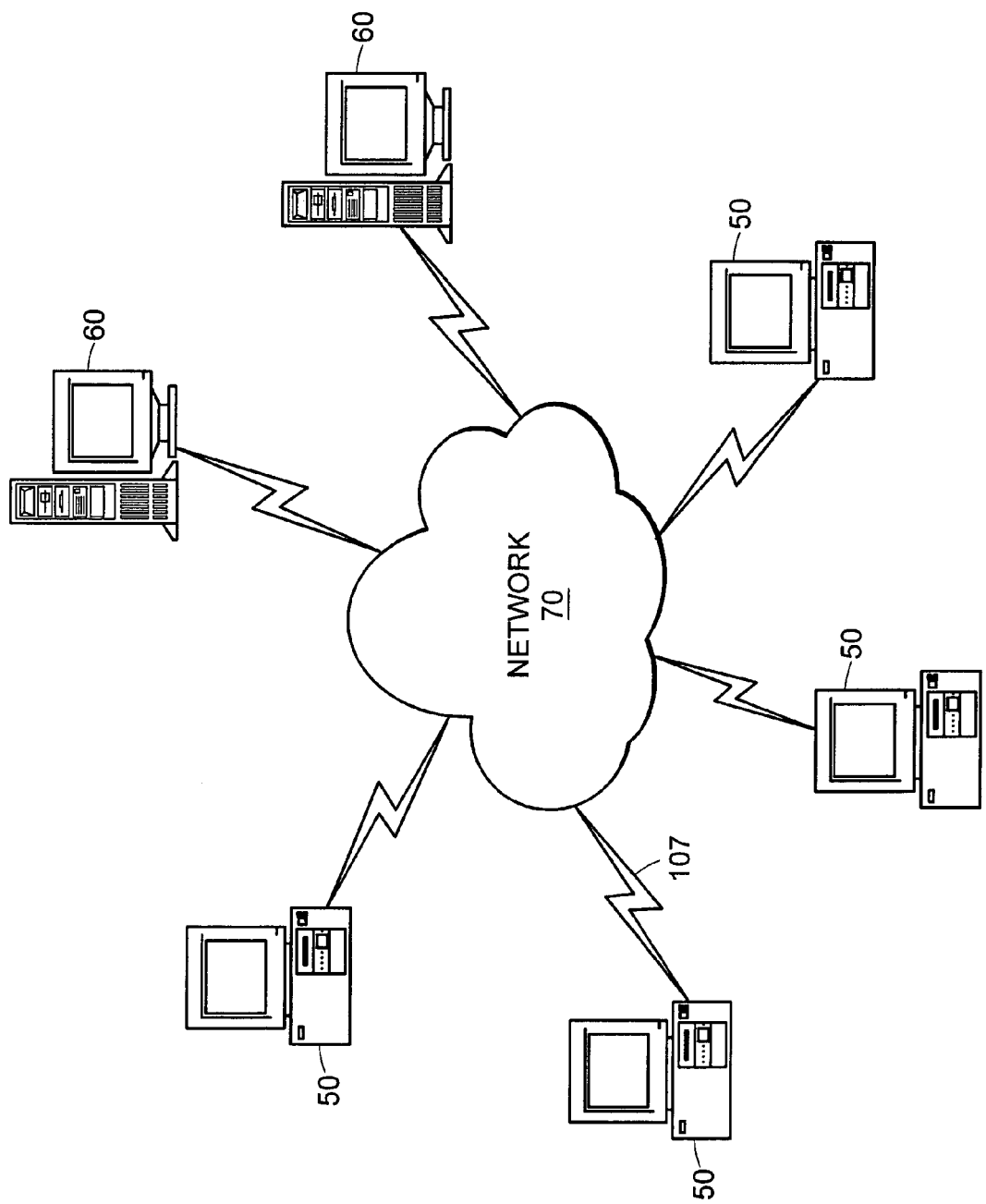
FIG. 1 is a schematic illustration of a computer network environment in which embodiments of the present invention may be practiced.

FIG. 1 illustrates a computer network or similar digital processing environment in which the present invention may be implemented.

Client computer(s)/devices 50 and server computer(s) 60 provide processing, storage, and input/output devices executing application programs and the like. Client computer(s)/devices 50 can also be linked through communications network 70 to other computing devices, including other client devices/processes 50 and server computer(s) 60. Communications network 70 can be part of a remote access network, a global network (e.g., the Internet), a worldwide collection of computers, Local area or Wide area networks, and gateways that currently use respective protocols (TCP/IP, Bluetooth, etc.) to communicate with one another. Other electronic device/computer network architectures are suitable.

Figure 2:
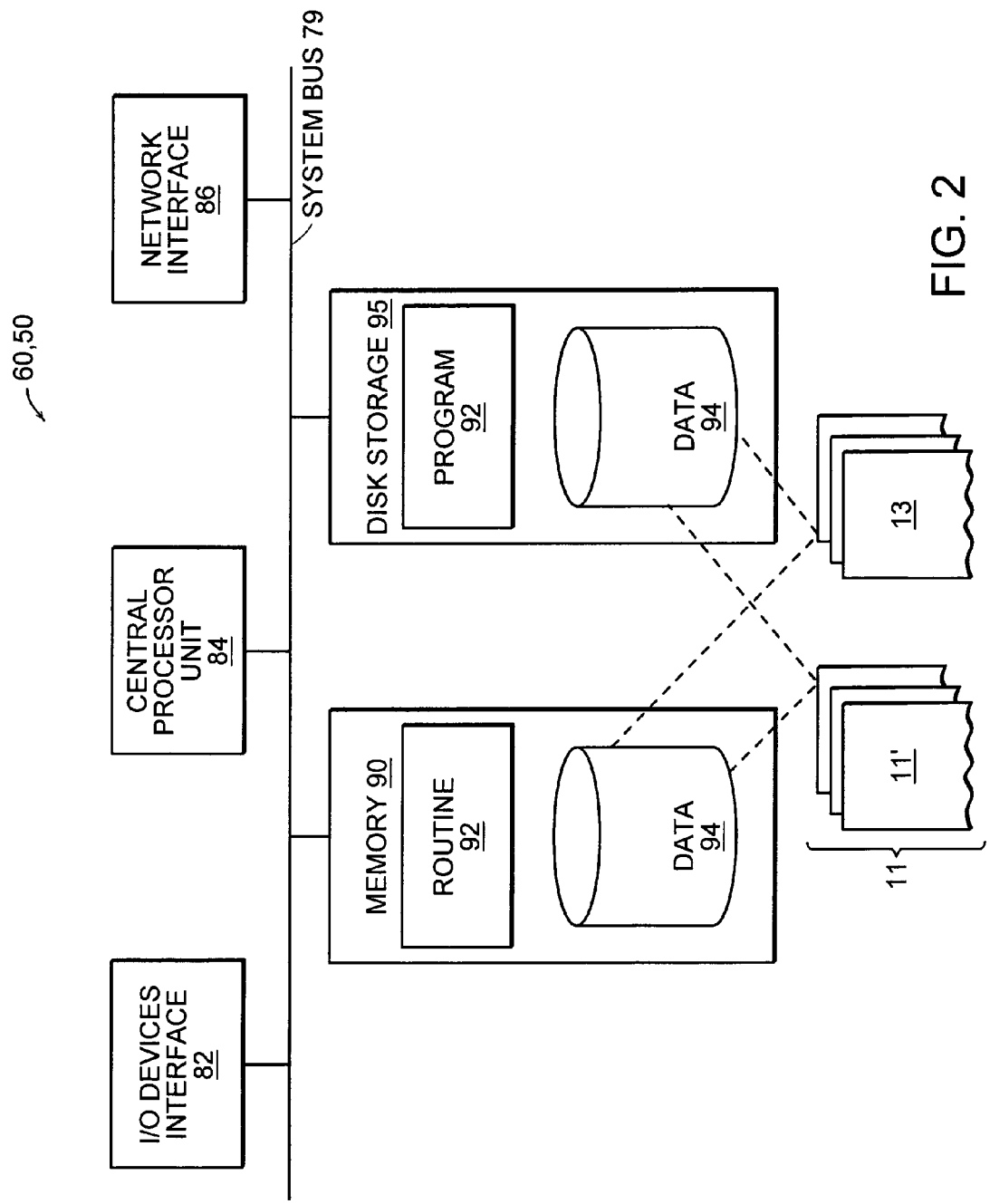
FIG. 2 is a block diagram of a computer from one of the nodes of the network of FIG. 1.

FIG. 2 is a diagram of the internal structure of a computer (e.g., client processor/device 50 or server computers 60) in the computer system of FIG. 1. Each computer 50, 60 contains system bus 79, where a bus is a set of hardware lines used for data transfer among the components of a computer or processing system. Bus 79 is essentially a shared conduit that connects different elements of a computer system (e.g., processor, disk storage, memory, input/output ports, network ports, etc.) that enables the transfer of information between the elements. Attached to system bus 79 is I/O device interface 82 for connecting various input and output devices (e.g., keyboard, mouse, displays, printers, speakers, etc.) to the computer 50, 60. Network interface 86 allows the computer to connect to various other devices attached to a network (e.g., network 70 of FIG. 1). Memory 90 provides volatile storage for computer software instructions used to implement an embodiment of the present invention (e.g., Program Routines 92 and Data 94, detailed later). Disk storage 95 provides non-volatile storage for computer software instructions 92 and data 94 used to implement an embodiment of the present invention. Central processor unit 84 is also attached to system bus 79 and provides for the execution of computer instructions. As will be made clear later, data 94 includes subject (original or observed) data 11 and working segment data 13.

In one embodiment, the processor routines 92 and data 94 are a computer program product (generally referenced 92), including a computer readable medium (e.g., a removable storage medium such as one or more DVD-ROM's, CD-ROM's, diskettes, tapes, etc.) that provides at least a portion of the software instructions for the invention system. Computer program product 92 can be installed by any suitable software installation procedure, as is well known in the art. In another embodiment, at least a portion of the software instructions may also be downloaded over a cable, communication and/or wireless connection. In other embodiments, the invention programs are a computer program propagated signal product 107 embodied on a propagated signal on a propagation medium (e.g., a radio wave, an infrared wave, a laser wave, a sound wave, or an electrical wave propagated over a global network such as the Internet, or other network(s)). Such carrier medium or signals provide at least a portion of the software instructions for the present invention routines/program 92.

In alternate embodiments, the propagated signal is an analog carrier wave or digital signal carried on the propagated medium. For example, the propagated signal may be a digitized signal propagated over a global network (e.g., the Internet), a telecommunications network, or other network. In one embodiment, the propagated signal is a signal that is transmitted over the propagation medium over a period of time, such as the instructions for a software application sent in packets over a network over a period of milliseconds, seconds, minutes, or longer. In another embodiment, the computer readable medium of computer program product 92 is a propagation medium that the computer system 50 may receive and read, such as by receiving the propagation medium and identifying a propagated signal embodied in the propagation medium, as described above for computer program propagated signal product.

Generally speaking, the term "carrier medium" or transient carrier encompasses the foregoing transient signals, propagated signals/medium, storage medium and the like.

Figure 3:
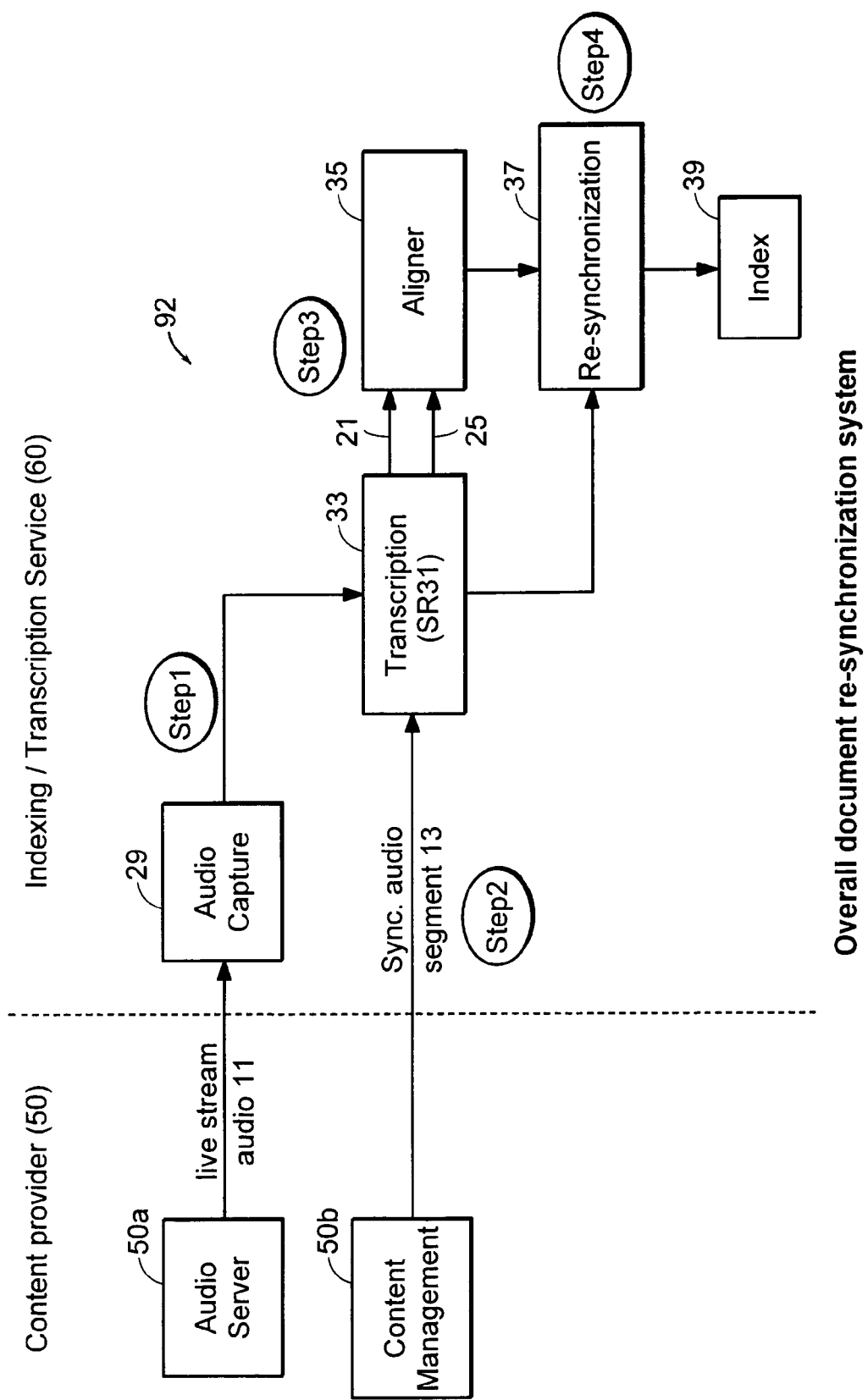
FIG. 3 is a schematic diagram of an audio/video indexing system according to the principles of the present invention.
Figure 4:
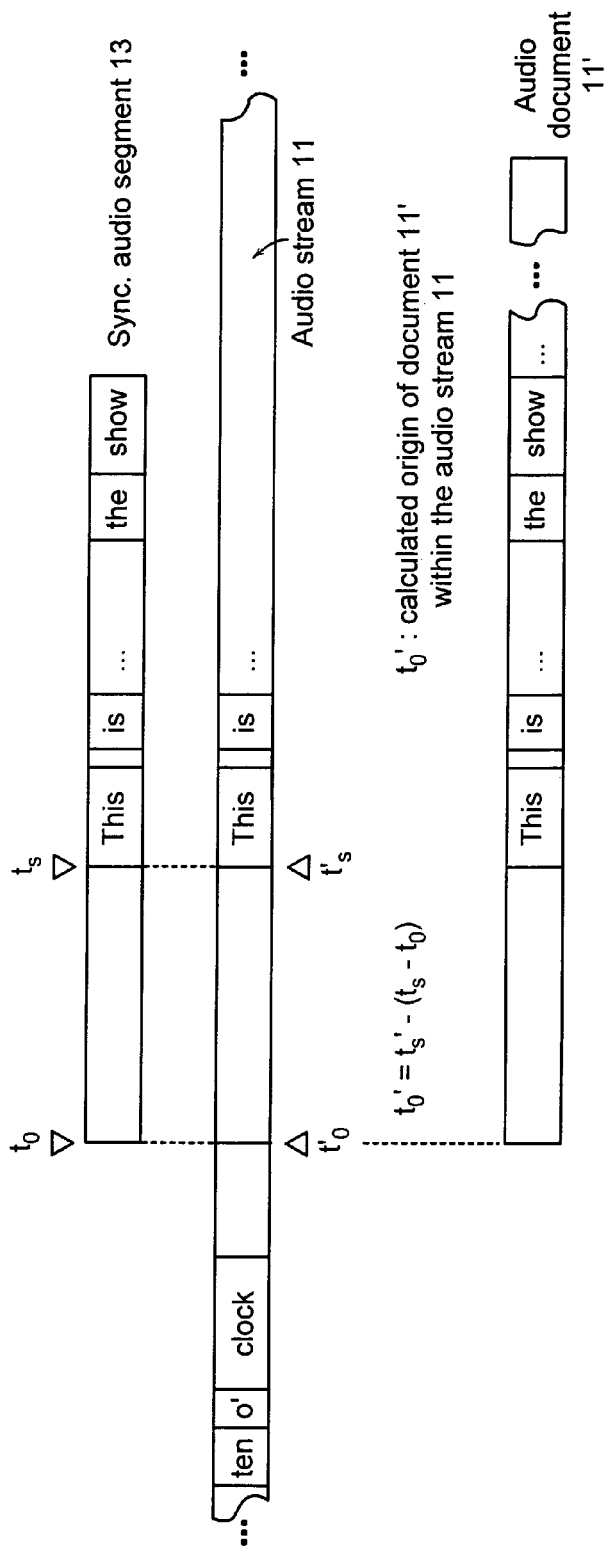
FIG. 4 is a detailed view of the alignment steps employed in the system of FIG. 3.

In one embodiment, a host server computer 60 provides a portal (services and means) for synchronizing data signals and routine 92 implements the invention data signal synchronization system. FIGS. 3 and 4 illustrate one such program 92 for data signal synchronizing services and means in a global computer network 70 environment. In the illustrated embodiment, the subject data signal 11 is streaming audio data from a content provider (such as a radio studio). The second data signal or working segment 13 is a specific portion (known in the art as a snippet) of the subject data signal 11 with corresponding radio show time (begin time) and show length. The present invention computer system or services 92 provide indexing or other time delineating/parameterizing of the streaming audio data 11 based on the stated show time (i.e., time parameters, generally) of the snippet (working segment) 13.

In particular, a speech recognizer 31 (of the type known in the art) transcodes audio data 11 into a textual transcription 21. Each word of the text transcription 21 is labeled with a time stamp measuring the time elapsed since the beginning of the audio data stream 11 capture, to the beginning of the word. The text transcription 21 is then used to index a source audio document 11' (portion of original data stream 11), which can be searched with text queries.

The audio document capture 29, transcription 33, re-synchronization 37 and indexing 39 processes are further described next as illustrated in FIGS. 3 and 4.

Step 1—real time live audio transcription.

In the audio capture process 29, the invention system 92 captures continuously the incoming audio data packets from a live audio data stream 11 (from an audio server 50a, for example) and sends the packets to a transcription module 33. The transcription module 33 employs the speech recognizer 31 and produces in turn a stream of time coded words. The stream of time coded words forms text output 21.

The audio capture subsystem 29 has no knowledge of the content of the subject audio data 11. Although most audio streaming protocols could embed timing information, this information is usually not present, thus the need for the present invention.

Applicants assume that the transcription module 33 processes audio data 11 in real time with possibly some latency. The latency is usually introduced by the packetization of the incoming audio data 11 and the processing of the audio data by the speech recognition 31/transcription module 33. As a result, the text output 21 may be delayed by a few minutes or some period of time.

Alternatively, the audio data stream 11 may be processed only for limited periods of time when shows of interest are broadcast. In that case, the content provider 50 sends a begin document message which contains the URL of the live stream, the identification of the document and an indication of the time of the beginning of the document. The start recording time is not an exact time since time synchronization cannot be achieved accurately on streaming data. To be conservative, the recording by audio capture processing 29 and transcription module 33 will actually start a few seconds before the time specified by content provider 50. System clocks are used to start and end the recording. Systems clocks can be synchronized with a GPS (global positioning system) clock. It is important to note that a delay is introduced by the audio capture component 29 which needs to buffer the incoming audio 11. A 30 second buffer is common.

In any case, Applicants assume that the recorded audio data 11 fully contains the show (source audio document 11') to be archived and indexed.

Next, one needs to locate precisely the start time and end time of the show within the live data stream 11.

Step 2—start and end time specification.

In order to specify the start and end time of a show, the content provider 50 (through a content management subsystem 50b, for example) sends a synchronization audio segment (working segment) 13. The origin of the synchronization audio segment 13 corresponds to the beginning or to the end of the source audio document 11' to be indexed.

The synchronization audio segment 13 can be sent at any time after the beginning of the show broadcast. As soon as the location of the synchronization audio segment 13 in the live data stream 11 has been calculated, the (word) text transcription 21 time codes can be corrected on the fly (i.e., during transcription 33). Note however that the archived document 11' can be indexed only after a complete re-synchronization of the text transcription 21 has been performed.

The working segment 13 should be long enough so that it can be identified within the recorded audio data stream 11 (e.g., greater than 30 seconds for audio applications).

Step 3—calculate start and end time.

The start and end times are calculated by matching the synchronization/working audio segment 13 with the recorded audio data stream 11.

The audio matching can be done in different ways. However, since the audio may be encoded at different rates and with different audio coding/decoding, it is not possible to compare the audio samples 11 and 13 directly. In order to achieve robust matching, Applicants use audio features instead. Different kinds of audio features can be used, such as melcep coefficient vectors, phoneme strings or word transcriptions. The preferred implementation described below uses a word transcription.

The audio matching method proceeds as follows (see FIG. 4).

Step 3a. The synchronization/working audio segment 13 is transcribed with the same speech recognition engine 31 used to process the live data stream 11. The result is a synchronization text string 25.

Step 3b. The synchronization text string 25 is aligned with the streaming data text transcription 21 in order to identify the exact point in time (and hence location in data stream 11) of the beginning of the source audio document 11'.

Classical dynamic programming techniques can be used to accurately align the synchronization text 25 with the subject data stream text transcription 21. Once the synchronization text 25 is aligned, the time code of any of the words in text transcript 21 gives the time offset between the document 11' and the recorded live stream 11.

If $t_s$ is the start time of word $w_i$ within the synchronization text 25 (of working segment 13), and $t'_s$ is the time of the corresponding word $w'_i$ within the streamed text transcription 21 (of subject stream data 11), then the origin of the source audio document 11' within the subject data stream 11 is given by the formula $t'_0=t'_s-t_s$ or $t'_0=t's-(t_s-t_0)$ for nonzero origin $t_0$ of working segment 13 (synchronization text 25). The time offset (amounts of time between time coded words of text transcript 21) can then be used to re-synchronize 37 the whole text transcription 21 of the source audio document 11'. So, time of appearance of a word in document 11' is time offset for that word in text transcript 21 minus $t'_0$.

Thus the re-synchronizing 37 is by effectively transposing the time system of the working segment 13 (synchronization text 25) onto the subject data stream 11 (text transcription 21).

In order to limit the search space, the content provider 50 may send as part of the working segment 13 indications of the approximate start time and duration of the show. The alignment process 35 then starts from the approximate start time, and ends when the synchronization string 25 matches the streamed text transcription 21.

Step 4—re-synchronize transcription.

Returning to FIG. 3, alternatively, the content provider 50 can specify the exact duration of the show so the end synchronization audio segment 13 of step 3 is no longer needed. The show duration can be used to stop the audio capture 29. The system 92 makes sure there is enough audio recorded for the whole document 11'. The text transcription 21 is then clipped to the proper length using the time code information on words. The source audio document 11' is then ready for indexing 39 shortly after the end of the live broadcast. Words in document 11' are then indexed according to time of appearance (calculated per word above). In this manner, the time coordinates of the working segment 13 are transposed onto the subject data signal 11 and hence onto document 11' of interest.

Given the foregoing, it is understood that a date/time code may be employed instead of just an hours/minutes time code. Likewise, other parameters or coordinates besides time may be employed. Further, it is understood that the subject streaming data 11 may be video or multimedia, although audio is used in the foregoing description by way of illustration and not limitation on the present invention. In general terms, the present invention synchronizes the subject data signal 11 to the coordinate (e.g., time) system of the working segment 13.

The main advantages of the present invention are:
it does not require external clock synchronization,
it is only based on content,
it does not require a specialized protocol for time synchronization,
it does not require a synchronization signal.

Applicants' method has the main advantage of being general and does not require either specialized protocols or programs for synchronization at the time of the broadcast. Applicants' approach is effective when the synchronization is performed after reception and storage of the source data stream.

While this invention has been particularly shown and described with references to preferred embodiments thereof, it will be understood by those skilled in the art that various changes in form and details may be made therein without departing from the scope of the invention encompassed by the appended claims.

For example, the present invention also addresses the problem of synchronization of multiple recordings of the same data source. Although the primary intent/use of the invention is to re-synchronize live and archived audio/video streams, it is a general purpose method that can be used in very different domains. For instance, two streaming physiological data signals, e.g., electrocardiogram (ECG) signals, recorded on a same patient with two different devices or in two different systems may need to be re-synchronized. If the recorders cannot use external clock synchronization, the streaming physiological/ECG data may be significantly off. Even if the device clocks are synchronized, the respective physiological ECG signals may be off by a fraction of a second. Signal analysis may require high precision synchronization, in the order of 1/100 second. The same approach described above can be used to accurately align the two physiological/ECG signals. A "transcription" (generally, a transformation to a common representation) of the signals is computed and then aligned using dynamic programming techniques. In the case of ECG signals, the common representation can be a string of beat interval time durations.

Figure 5:
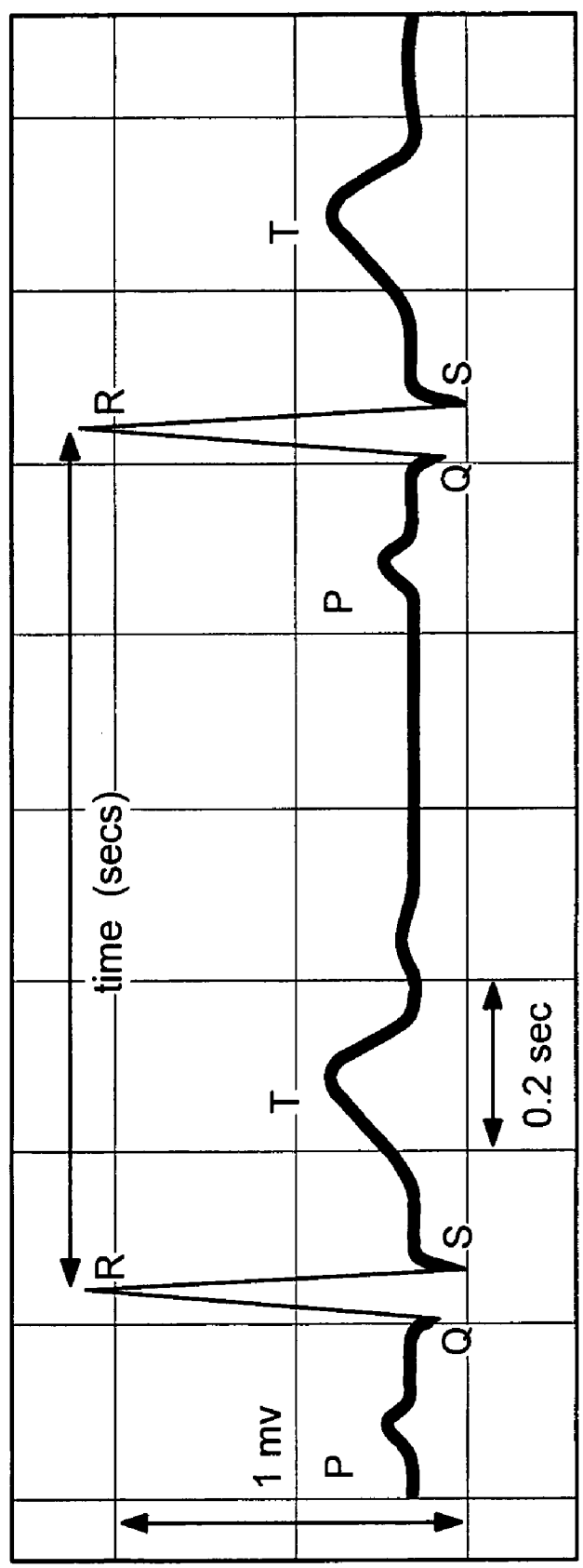
FIG. 5 is a schematic illustration of an electrocardiogram.

As illustrated in FIG. 5, an electrocardiogram is a graphical representation of the electrical activity of the heart plotted along a time axis. A typical electrocardiogram consists of a regular sequence of waves, the P, QRS, and T waves. The P wave is generated by the contraction of the atria. Contraction of the ventricles generates the QRS wave complex. And the T wave is generated by the relaxation of the ventricles. Amplitude of each of these components (waves) depends on the orientation of the heart within the individual and which electrodes are used to record the ECG. Distance between the R waves in a given signal is variable. When an ECG is performed, it is common to measure the heart rate for several cardiac cycles to determine how consistently the heart beats. In addition to doctors analyzing whether the interval between waves from consecutive cardiac cycles remain consistent, doctors also look for how fast the heart is beating, consistent shape of each wave, and normality of duration and configuration of each wave.

The heart rate is the number of times the heart beats per minute which can be calculated by counting the average number of beats for a given duration (typically 15-30 seconds). The linear distance between neighboring peaks of simultaneous heart beats on an ECG corresponds to the time necessary for a single cardiac cycle (heart beat). As illustrated in FIG. 5, the linear distance is measured between the peaks of neighboring QRS waves.

Applying the present invention, the linear distance between R peaks is computed for a first device ECG signal of a patient and forms a subject string of beat interval time durations. The distance between R peaks is computed for the ECG signal from a different (second) device used on the same patient and forms a working string of beat interval time durations. The subject string and working string are aligned or otherwise matched to each other. The time coordinates of the working string are transposed onto the subject string such that the ECG signal of the first device is synchronized to the time system of the other (second) device. That is, time intervals of waves in the first device ECG signal are set equal to time intervals of corresponding waves of second device ECG signal.

This is especially useful to diminish the effects of noise in the first device ECG signal where the second device ECG signal is relatively less noisy. Other signal qualities may be similarly compensated for.

In other embodiments, other series of data/signals 11, 13 are employed. Where the subject signal 11 is a sample genomic sequence, the working segment 13 is a genomic sequence of a known medical condition. The genomic sequence of the working segment 13 has predefined markers. The transformation 33 to a common representation and alignment 35 include expressing the sample genomic sequence 11 with respect to the markers of the genomic sequence of the working segment 13. The re-synchronization or step of transposing 37 then includes determining subsequences of the sample genomic sequence 11 to be equivalent to subsequences of the working segment 13 in terms of the known medical condition.

These and other domains may apply the principles of the present invention as disclosed herein.

In another example, other coordinates and other coordinate systems (besides time) are suitable. The foregoing discusses resynchronization based on time coordinates of the working segment. Approximate location of the working segment within the subject signal may also similarly be employed.

What is claimed is:

1. A method of synchronizing one data signal with another data signal, comprising the computer implemented steps of:
   receiving one data signal as a subject signal;
   receiving another data signal as a working segment, the working segment including predefined coordinates in a coordinate system;
   transforming the subject signal and working segment into a common representation, said transforming resulting in respective transformed representations of the subject signal and working segment;
   aligning the respective transformed representations by matching the transformed representation of the working segment and the transformed representation of the subject signal to each other, said aligning producing an aligned state of the respective transformed representations; and
   transposing, by a processor of a computing device, the predefined coordinates of the working segment onto the subject signal in the aligned state of the respective transformed representations, such that the subject signal is synchronized to the coordinate system of the working segment,
   wherein one of:
      the subject signal is streaming physiological data of a patient taken by one medical system, the working segment is streaming physiological data of the same patient taken by a different medical system and having relatively better qualities than the subject signal, the step of transforming includes determining a string of beat interval time durations in the subject signal and determining a respective string of beat interval time durations in the working segment, the step of aligning includes matching the respective determined string representations of the subject signal and the working segment to each other, and the step of transposing includes setting time intervals of a subset of waves in the subject signal equal to time intervals of waves of the working segment effectively compensating for qualities lacking in the subject signal;
      the subject signal is a sample genomic sequence, the working segment is a genomic sequence of a known medical condition and having predefined markers the step of transforming and aligning includes expressing the sample genomic sequence with respect to the markers of the genomic sequence of the working segment, and the step of transposing includes determining subsequences of the sample genomic sequence to be equivalent to subsequences of the working segment in terms of the known medical condition.

2. A method as claimed in claim 1 wherein:
   the streaming physiological data is ECG (electrocardiograph) data; and
   the string of beat interval time durations employed in the steps of transforming and aligning includes distances between R waves.

3. A method as claimed in claim 1 further comprising the step of indexing the subject signal according to the coordinate system of the working segment.

4. A method as claimed in claim 1 wherein the transformed representations of the subject signal and working segment include features that are matched between the subject signal and working segment during said aligning step.

5. A method as claimed in claim 4 wherein the features comprise text and individual words are matched between the subject signal and working segment during said aligning step.

6. A method as claimed in claim 4 wherein a dynamic programming technique is used to align features in the subject signal with features in the working segment.

7. A method as claimed in claim 4 wherein the aligning step identifies a time offset between time codes in the subject signal and time codes in the working segment.

8. A method as claimed in claim 7 wherein the time offset is used to adjust the time codes in the subject signal.

9. A method as claimed in claim 1 wherein the subject signal and the working segment comprise different recordings of a single data source.

10. A system for synchronizing one data signal to another data signal, comprising:
    hardware;
    means for receiving a subject signal;
    means for receiving a working segment, the working segment having predefined coordinates in a coordinate system;

transformation means for transforming the received subject signal and received working segment into a common representation such that respective transformed representations of the subject signal and working segment result;

alignment means for aligning the respective transformed representations; and re-synchronization means for receiving from the alignment means the aligned respective transformed representations, and for transposing the predefined coordinates of the working segment onto the subject signal, such that the subject signal is synchronized to the coordinate system of the working segment, wherein one or more of the means for receiving the subject signal, the means for receiving the working segment, the transformation means, the alignment means, and the re-synchronization means are implemented at least by the hardware, and wherein one of:

the subject signal is streaming physiological data of a patient taken by one medical system, the working segment is streaming physiological data of the same patient taken by a different medical system and having relatively better qualities than the subject signal, the transformation means determines a string of beat interval time durations in the subject signal and determines a respective string of beat interval time durations in the working segment, the alignment means matches the respective determined string representations of the subject signal and the working segment to each other, and the re-synchronization means sets time intervals of a subset of waves in the subject signal equal to time intervals of waves of the working segment, effectively compensating for qualities lacking in the subject signal;

the subject signal is a sample genomic sequence, the working segment is a genomic sequence of a known medical condition and having predefined markers, the transformation means and alignment means express the sample genomic sequence with respect to the markers of the genomic sequence of the working segment, and the re-synchronization means determines subsequences of the sample genomic sequence to be equivalent to subsequences of the working segment in terms of the known medical condition.

11. A system as claimed in claim 10 wherein:
the streaming physiological data is ECG (electrocardiograph) data; and
the string of beat interval time durations includes distances between R waves.

12. A system as claimed in claim 10 further comprising indexing means for indexing the subject signal according to the coordinate system of the working segment.

13. A method comprising:
receiving a subject data signal, the subject data signal comprising a first data signal portion and a second data signal portion, a desired data signal being the second data signal portion in its entirety;
receiving a working data signal, the working data signal being a portion of the second data signal portion of the subject data signal less than the second data signal portion in its entirety, the working data signal being a portion of the desired data signal less than the desired data signal in its entirety, an origin of the working data signal corresponding to a beginning of the desired data signal; and locating the beginning of the desired data signal within the subject data signal, by a processor of a computing device matching the origin of the working data signal to a corresponding location within the subject data signal to synchronize the working data signal to the subject data signal, where matching the origin of the working data signal to the corresponding location within the subject data signal comprises matching an audio feature of the working data signal to a corresponding audio feature of the data signal;

wherein matching the audio feature of the working signal to the corresponding audio feature of the subject data signal further comprises:
transforming the subject data signal to yield a plurality of subject melcep coefficient vectors;
transforming the working data signal to yield a plurality of working melcep coefficient vectors; and
locating the working melcep coefficient vectors within the subject melcep coefficient vectors to find the corresponding location within the subject data signal that matches the origin of the working data signal.

14. The method of claim 13, wherein matching the origin of the working data signal to the corresponding location within the subject data signal further comprises determining the origin of the working data signal within the subject data signal via $t'_0 = t'_s - (t_s - t_0)$, where $t_0$ is the origin of the working data signal where the origin is non-zero, $t_s$ is a location of the corresponding audio feature within the subject data signal, $t'_0$ is the corresponding location within the origin of the working data signal within the subject data signal, and $t'_s$ is a location of the audio feature of the working data signal within the subject data signal.

15. The method of claim 13, wherein matching the origin of the working data signal to the corresponding location within the subject data signal further comprises determining the origin of the working data signal within the subject data signal via $t'_0 = t'_s - t_s$, where the origin of the working data signal is zero, $t_s$ is a location of the corresponding audio feature within the subject data signal, $t'_0$ is the corresponding location of the origin of the working data signal within the subject data signal, and $t'_s$ is a location of the audio feature of the working data signal within the subject data signal.

16. The method of claim 13, wherein matching the audio feature of the working data signal to the corresponding audio feature of the subject data signal further comprises:
transcribing the subject data signal to yield a subject data signal textual transcription;
transcribing the working data signal to yield a working data signal textual transcription; and,
locating the working data signal textual transcription within the subject data signal textual transcription to find the corresponding location within the subject data signal that matches the origin of the working data signal.

17. The method of claim 13, wherein matching the audio feature of the working data signal to the corresponding audio feature of the subject data signal further comprises:
processing the subject data signal to yield a plurality of subject phoneme strings;
processing the working data signal to yield a plurality of working phoneme strings;
locating the working phoneme strings within the subject phoneme strings to find the corresponding location within the subject data signal that matches the origin of the working data signal.

* * * * *

UNITED STATES PATENT AND TRADEMARK OFFICE
CERTIFICATE OF CORRECTION

PATENT NO.        : 7,627,811 B2                                        Page 1 of 1
APPLICATION NO.   : 11/072036
DATED             : December 1, 2009
INVENTOR(S)       : Jean-Manuel Van Thong et al.

It is certified that error appears in the above-identified patent and that said Letters Patent is hereby corrected as shown below:

In column 8, line 22, in Claim 1, delete "segment" and insert -- segment, --, therefor.

In column 8, line 26, in Claim 1, delete "markers" and insert -- markers, --, therefor.

In column 9, line 66, in Claim 13, delete "and" and insert -- and, --, therefor.

In column 10, line 10, in Claim 13, after "the" insert -- subject --.

Signed and Sealed this

Twenty-third Day of March, 2010

David J. Kappos
*Director of the United States Patent and Trademark Office*